United States Patent [19]

Steinacker et al.

[11] 4,173,581

[45] Nov. 6, 1979

[54] PROCESS FOR THE PREPARATION OF ALKYLTHIOSEMICARBAZIDES

[75] Inventors: Karl-Heinz Steinacker; Gerhard Adolphen, both of Leverkusen, Fed. Rep. of Germany

[73] Assignee: Bayer Aktiengesellschaft, Leverkusen, Fed. Rep. of Germany

[21] Appl. No.: 904,346

[22] Filed: May 9, 1978

[30] Foreign Application Priority Data

May 23, 1977 [DE] Fed. Rep. of Germany ....... 2723121

[51] Int. Cl.² .......................................... C07C 159/00
[52] U.S. Cl. .............................. 260/552 SC; 260/567
[58] Field of Search .......................... 260/552 SC, 567

[56] References Cited

U.S. PATENT DOCUMENTS

| | | | |
|---|---|---|---|
| 3,193,580 | 7/1965 | Werres et al. | 260/567 |
| 3,255,251 | 6/1966 | Budd | 260/567 |
| 3,661,983 | 5/1972 | Nash | 260/567 X |
| 4,132,736 | 1/1979 | Cramm et al. | 260/552 SC |

FOREIGN PATENT DOCUMENTS

| | | | |
|---|---|---|---|
| 138018 | 8/1970 | Czechoslovakia | 260/552 SC |
| 83559 | 8/1971 | German Democratic Rep. | 260/552 SC |
| 1032639 | 7/1953 | France | 260/552 SC |

*Primary Examiner*—Thomas A. Waltz
*Attorney, Agent, or Firm*—Sprung, Felfe, Horn, Lynch & Kramer

[57] ABSTRACT

A process for preparing an alkylthiosemicarbazide of the formula

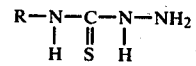

wherein
R represents an alkyl group having up to 4 carbon atoms by contacting a dialkylthiouram disulfide of the formula

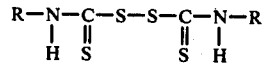

wherein
R represents an alkyl group having up to 4 carbon atoms with hydrazine in an aqueous medium.

6 Claims, No Drawings

PROCESS FOR THE PREPARATION OF ALKYLTHIOSEMICARBAZIDES

The invention relates to a new process for the preparation of an alkylthiosemicarbazide by reacting a dialkylthiuram disulphide with hydrazine.

Processes for the preparation of alkylthiosemicarbazides are already known, for example methylthiosemicarbazide is obtained in the reaction of methyl mustard oil with hydrazine (Houben Weyl, Methoden der organischen Chemie (Methods of Organic Chemistry), Volume IX (1955), page 908).

It has now been found that an alkylthiosemicarbazide of the formula

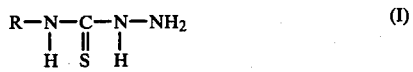

in which
R denotes alkyl having up to 4 carbon atoms, is obtained in a simple manner if a N,N'-dialkylthiuram disulphide of the formula

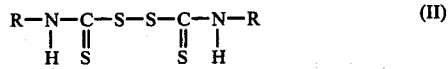

in which
R has the meaning indicated above, is reacted with hydrazine in an aqueous medium.

In general the reaction is carried out within the temperature range from about 20° to 100° C., but is preferably carried out within the temperature range from 30° to 70° C.

Straight-chain and branched alkyl radicals are possible as alkyl having up to 4 carbon atoms; the following may be mentioned as examples: methyl, ethyl, propyl, isopropyl, butyl, isobutyl and tert.-butyl. R preferably represents methyl and ethyl.

The N,N'-dialkylthiuram disulphide of the formula (II) which is used as the starting compound, and the preparation thereof, has been known for a long time (Berichte, Volume 35 (1902), pages 816 to 830, in particular page 821).

Hydrazine can be employed as such, in the form of hydrazine hydrate or in aqueous solution, in particular at a concentration of 10 to 100% by weight of hydrazine. It is preferable to use commercially available hydrazine hydrate or commercially available aqueous hydrazine solutions having a content of 50 to 100% by weight of $NH_2NH_2$.

At least the theoretically required quantity of 2 mols of hydrazine is employed per mol of dialkylthiuram disulphide of the general formula (II), but an excess of hydrazine over the theoretically required quantity is advantageous.

In general, an excess of at least up to 5% of hydrazine is used, although no upper limit is set to the excess of hydrazine. It is appropriate, for economic reasons, not to select too high an excess of hydrazine.

It is preferable to use an excess of hydrazine of five to fifty percent of the theoretically required quantity, that is, 2.1 to three mols of hydrazine per mol of disulphide of the formula (II).

Using methylthiosemicarbazide as an example, the process according to the invention may be illustrated, for example, by the equation below

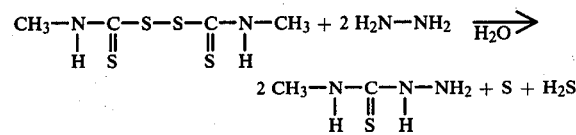

The process according to the invention is simple to carry out. In general, the dialkylthiuram disulphide of the formula (II), in aqueous solution or suspension, is taken and the hydrazine, optionally in aqueous solution, is then added.

In general, 0.5 to 5, preferably 1 to 3, ml of water are used per g of dialkylthiuram disulphide for the preparation of the aqueous reaction medium.

The quantity of hydrazine required can be added to the aqueous solution or suspension of the disulphide of the formula (II) all at once, at the beginning of the reaction, and the reaction mixture can then be heated to the reaction temperature. One can, however, first heat the aqueous solution or suspension of the disulphide of the formula (II) to the reaction temperature selected and then add the hydrazine.

It can be particularly advantageous here to add the hydrazine in accordance with its consumption in the reaction, which takes place with a positive heat change, and thus, simultaneously, to influence the reaction temperature.

As already mentioned above, the reaction according to the invention can be carried out within the temperature range from about 20° to 100° C. In order not to necessitate too long reaction times, it is appropriate to carry out the reaction within the temperature range from 30° to 70° C. This ensures that, on the one hand, the reaction does not proceed too slowly, but also, on the other hand, does not proceed so rapidly that it gets out of control. It can optionally be advantageous to arrange for the removal of the excess heat of reaction by cooling and thus to maintain the reaction temperature selected, unless, under given conditions, without an external supply of heat, the heat loss compensates for the resulting heat of reaction.

The hydrogen sulphide which is produced as a byproduct remains, dissolved in the form of a salt, in the reaction mixture; some of it reacts with hydrazine to give ammonia and sulphur. Ammonia which is formed reacts to give ammonium sulphide, which dissolves some of the sulphur with the formation of red to brown ammonium polysulphides. These polysulphides can be destroyed by oxidation with air or can be decomposed, by acidification, into ammonia, sulphur and hydrogen sulphide. The last-mentioned can be expelled by being blown out or by heating and can be collected in a known manner by means of alkali metal hydroxide solution or can be destroyed by combustion. The second by-product, sulphur, remains in the reaction mixture and can be removed from the hot reaction solution after the completion of the reaction and supplied to other uses in a known manner.

The resulting alkylthiosemicarbazide can be isolated from the reaction solution in a known manner, for example, by being crystallised out and filtered off.

The residual mother liquor can either be discarded or can be used again, instead of water, in the reaction according to the invention. By these means it is then also unnecessary to recover the unreacted excess hydrazine remaining in this mother liquor, and the amount of hydrazine used in the reaction according to the invention can be reduced correspondingly.

In general, only a few by-products are formed in the reaction according to the invention.

The process according to the invention can, therefore, be carried out advantageously by again adding the starting materials in a suitable ratio to the residual reaction medium subsequent to the separation of the sulphur and, subsequently, of the alkylthiosemicarbazide which is formed, and carrying out the reaction again. In the course thereof, it is only necessary to make up the unavoidable losses of water, but, advantageously, no effluent is produced.

If desired, this cyclic process can, of course, also be developed in a known manner to give a fully continuous process.

The particular advantage of the process according to the invention is based on the fact that no unutilisable byproducts are produced, the starting materials are readily accessible and, from a long-term point of view, virtually no effluent, or only a little, is produced. The process according to the invention thus causes particularly little environmental pollution.

Alkylthiosemicarbazides are valuable organic intermediate products. They can, for example, be reacted with carbonyl compounds to give thiosemicarbazones, which are used as protective agents against the sun, U.S. Pat. No. 3,923,681 (CA 84, 135,651). They can be used as a starting material for herbicides, DOS (German Published Specification) 2,404,979 (CA 83, 189,333) or they can even be used as insecticides, Jap. Kokai 75, 145,525 (CA 84, 70,360).

EXAMPLE 1

55 g (1.1 mols) of hydrazine hydrate are added dropwise to 106 g (0.5 mol) of dimethylthiuram disulphide in 200 ml of water. The mixture is warmed to 50° C. and is stirred for 2 hours at this temperature. The precipitated sulphur (16 g) is then filtered off, the mixture is cooled to 10° C., the precipitated methylthiosemicarbazide (83 g) is filtered off and the product is washed with 50 ml of ice-cold water. The combined filtrates are acidified to pH 5 with 27 ml of concentrated hydrochloric acid. The hydrogen sulphide liberated (9.5 g) is blown out with nitrogen into sodium hydroxide solution. Precipitated sulphur (5 g) is filtered off. The filtrate is evaporated to dryness in vacuo. The residue (24.5 g) is dissolved in 50 ml of hot (90° C.) water, 1.5 g of sulphur are filtered off and the filtrate is cooled to 10° C. 8 g of product are precipitated. The filtrate is concentrated to 20 ml, adjusted to pH 9 with sodium hydroxide solution and cooled, a further 4.5 g of product being produced. Altogether, 95.5 g (=90.8% of theory) of methylthiosemicarbazide are obtained, with a melting point of 135°–7° C.

EXAMPLE 2

106 g (0.5 mol) of dimethylthiuram disulphide in 200 ml of water are stirred with 55 g (1.1 mols) of hydrazine hydrate for 2 hours at 50° C. 15 g of sulphur are then filtered off at this temperature. The filtrate is concentrated to dryness on a waterbath. In the course thereof, the colour changes from red-brown to yellow-grey. The residue is dissolved under hot conditions in 200 ml of water and 7.6 g of sulphur are filtered off. After cooling to 10° C., the solution gives 85 g of product. A further 12 g are obtained after concentrating the filtrate to 50 ml. The yield of methylthiosemicarbazide is 97 g (=92.4% of theory), with a melting point of 135°–137° C.

EXAMPLE 3

74.4 g (0.31 mol) of diethylthiuram disulphide, 150 ml of water and 50 g of hydrazine hydrate were stirred for 2 hours at 50° C. The sulphur formed was filtered off whilst hot, and the reaction solution was worked up as described in Example 2.

63.5 g (85.0% of theory) of ethylthiosemicarbazide of melting point 79° to 81° C. were obtained.

EXAMPLE 4

55 g of hydrazine hydrate were added to 106 g of dimethylthiuram disulphide in 200 ml of water and the mixture was warmed to 30° C. and stirred at this temperature for 5 hours. Sulphur was then filtered off whilst hot and the solution was worked up as described in Example 2.

The yield was 91.0 g (86.5% of theory) of methylthiosemicarbazide.

EXAMPLE 5

55 g of hydrazine hydrate were added to 106 g of dimethylthiuram disulphide in 200 ml of water and the mixture was warmed to 70° C. and stirred at this temperature for 40 minutes. Sulphur was then filtered off whilst hot, and the solution was worked up as described in Example 1. The yield was 95.0 g (90.5% of theory) of methylthiosemicarbazide.

EXAMPLE 6

130 g of dimethylthiuram disulphide in 200 ml of water were stirred with 75 g of hydrazine hydrate for 2 hours at 50° C. The sulphur formed was then filtered off at 50° C., the filtrate was cooled to 10° C. and the reaction product which had precipitated was filtered off.

A further 130 g of dimethylthiuram disulphide and 75 g of hydrazine hydrate were added to the mother liquor thus obtained, the mixture was again stirred for 2 hours at 50° C. and sulphur and the reaction product which had been formed were subsequently filtered off as described above.

A further 130 g of dimethylthiuram disulphide and 75 g of hydrazine hydrate were added to the mother liquor obtained, the mixture was stirred for 2 hours at 50° C. and the sulphur which had been formed and the reaction product were subsequently separated off as described above and the resulting mother liquor was employed again.

Altogether, 780 g of dimethylthiuram disulphide and 450 g of hydrazine hydrate were reacted in this way, in 6 batches, each time re-using the mother liquor, that is to say the aqueous reaction medium and the unconverted starting materials remaining in it.

The mother liquor was then worked up by concentration as in Example 2.

The total yield was 701.0 g (91.2% of theory) of methylthiosemicarbazide.

What is claimed is:

1. A process for preparing an alkylthiosemicarbazide of the formula

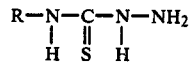

wherein
R is an alkyl group having up to 4 carbon atoms which comprises contacting a dialkylthiouram disulfide of the formula

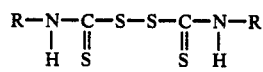

wherein
R is an alkyl group having up to 4 carbon atoms with hydrazine in an aqueous medium.

2. A process according to claim 1 wherein hydrazine is employed in an excess over the stoichiometrically required quantity of 2 mols hydrazine per mol of dialkylthiouram disulfide.

3. A process according to claim 1 wherein the reaction is carried out within the temperature range of from 20° to 100° C.

4. A process according to claim 1 wherein following the reaction the reaction products are separated off and the mother liquor is employed in a subsequent reaction as solvent therefor.

5. A process according to claim 3 wherein the reaction is carried out at a temperature from 30° to 70° C.

6. A process according to claim 1 wherein 0.5 to 5 ml of water are present in the reaction mixture per gram of dialkylthiouram disulfide.

* * * * *